US006986904B2

(12) United States Patent
Nilsson et al.

(10) Patent No.: US 6,986,904 B2
(45) Date of Patent: *Jan. 17, 2006

(54) FORMULATION

(75) Inventors: Hans Nilsson, Lund (SE); Gordon Santesson, Hörby (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/716,357

(22) Filed: Nov. 17, 2003

(65) Prior Publication Data

US 2004/0101486 A1 May 27, 2004

Related U.S. Application Data

(63) Continuation of application No. 09/933,974, filed on Aug. 20, 2001, now Pat. No. 6,686,346, which is a continuation of application No. 08/846,960, filed on Apr. 29, 1997, now Pat. No. 6,291,445.

(30) Foreign Application Priority Data

Dec. 5, 1996 (SE) .................................. 9604486

(51) Int. Cl.
*A61K 9/14* (2006.01)
(52) U.S. Cl. ..................... 424/489; 514/174; 514/951; 514/958
(58) Field of Classification Search ................ 424/489; 514/174, 951, 958
See application file for complete search history.

(56) References Cited

U.S. PATENT DOCUMENTS

| 3,992,534 | A | 11/1976 | Brattsand et al. ........... 424/421 |
| 5,509,404 | A | 4/1996 | Lloyd et al. ........... 128/200.14 |
| 6,291,445 | B1 * | 9/2001 | Nilsson et al. ............... 514/174 |
| 6,686,346 | B2 * | 2/2004 | Nilsson et al. ............... 514/174 |

FOREIGN PATENT DOCUMENTS

| WO | 97/01337 | 1/1997 |
| WO | 97/01341 | 1/1997 |

OTHER PUBLICATIONS

Arky, Physicians' Desk Reference, pp. 2301-2302, Medical Economics Co., Montvale, NJ 1997.

Arnon et al., "Delivery of Micronizeed Budesonide Suspension by Metered . . . A" Pediatr Pulmonol 13:172-175, Jul. 1992, Dialog Infor Sers, File 155, Medline, Dialog Acc No. 07274454, Medline Accession No. 93064921. Abstract Only.

Clissold, et al., "ADIS Drug Information Services," Drugs 2816: pp. 485-518 1984.

Clissold et al., "Budesonide A Preliminary Review of its Pharmacodynamic Properties and Therapeutic Efficacy in Asthma and Rhinitis", Drugs 28:485-518, 1994.

Creticos, et al., "Intranasal Budesonide Aqueos Pump Spray (Rhinocort® Aqua) for the Treatment of Seasonal Allergic Rhinitis", Allergy and Asthama Proc., pp. 285-294, vol. 19, No. 5, Sep.- Oct. 1998.

Malm et al., "Reduction of Metacholine-Induced Nasal Secretion by Treatment with a New Topical Steroid in Perennial Non-Allergic Rhinitis", Allergy 36:209-214, 1981.

Meltzer, "Clinical and anti-inflammatory effects of intranasal budesonide aqueous pump spray in the treatment of perennial allergic rhinitis", Anals of Allergy, Asthma & Immunology, pp. 128-134, vol. 81, Aug., 1998.

Pedersen, et al., "Budensonide Treatment of Moderate and Severe Asthma in Childrens", J. Alergy Clin. Immunol., 95:29-33, 1995, Abstract Only.

"Rhinocort® Nasal Inhaler", ASTRA USA, Inc., 09-081-16-0-80 (package insert, dated Jan. 1995), 2 pages.

"Rhinocort® Aqua", AB ASTRA Södertälje, Sweden, 09-089-62-097 (package insert, Aug. 1993), 2 pages.

"Rhinocort® Consumer Product Information", AB Astra (package insert, dated Jun., 1995), 3 pages.

"Patient Instructions About Rhinocort® Aqua" (package insert, Feb. 1993), 2 pages.

"Rhinocort® Aqua", ASTRA Pharma Inc. (Canada) (package insert, dated Aug. 1993), 2 pages.

"Patient Instructions About Rhinocort® Turbuhaler®", Astra Pharma Inc. (package insert, Oct. 1993), 3 pages.

"Rhinocort® Turbuhaler®", ASTRA Pharma Inc. (Canada) (package insert, dated Aug. 1993), 3 pages.

* cited by examiner

*Primary Examiner*—Sreeni Padmanashan
*Assistant Examiner*—Konata M. George
(74) *Attorney, Agent, or Firm*—Fish & Richardson P.C.

(57) ABSTRACT

A new metered unit dose comprising 40 µg or less of budesonide is disclosed as well as a formulation thereof and the use thereof for the treatment of conditions in the nose.

77 Claims, No Drawings

FORMULATION

CROSS-REFERENCE TO RELATED APPLICATIONS

This application is a continuation application of and claims priority to U.S. application Ser. No. 09/933,974 filed Aug. 20, 2001 now U.S. Pat. No. 6,686,346, which is a continuation application of Ser. No. 08/846,960, filed Apr. 29, 1997, now U.S. Pat. No. 6,291,445, which claims priority to Swedish Patent Application No. 9604486-2, filed Dec. 5, 1996, the contents of each being incorporated by reference herein.

FIELD OF THE INVENTION

The present invention relates to a new unit dose of budesonide, a formulation thereof, and its use for the treatment of conditions of the nose.

BACKGROUND OF THE INVENTION

Glucocorticosteroids are widely used for the treatment of seasonal allergic as well as perennial rhinitis. Intranasal glucocorticosteroids reduce inflammation of the nasal mucosa including edema. In addition, they are known to suppress the recruitment of polymorpho-nuclear and mono-nuclear cells, cytokine production, and, during maintenance treatment, both early and late-phase nasal reactions.

One of the glucocorticosteroids known for intranasal use is budesonide, $16\alpha,17\alpha$-butylidenedioxy-$11\beta,21$-dihydroxypregna-1,4-diene-3,20-dione.

Initially solid budesonide was used in pressurized metered dose inhaler (pMDI) preparations for intranasal administration, suitably dispensed from a specially adapted nasal inhaler. A recommended maximum daily metered dose of budesonide has been 400 $\mu$g. Later on a nasal spray preparation for delivery from a spray device was prepared, containing budesonide in the form of an aqueous suspension. The same maximum daily metered dose as for the pMDI preparation was recommended. A third formulation is a dry powder formulation.

Both the nasal pMDI inhaler device and the aqueous nasal spray device are constructed to dispense a defined unit dose at each actuation. For example, a metered unit dose of 50 $\mu$g has a recommended administration regime of one dose per nostril, four times daily, yielding a total of eight 50 $\mu$g metered doses per day. Alternatively, a metered unit dose of 100 $\mu$g would provide the same total metered daily dose (400 $\mu$g) if administered to each nostril twice daily, for a total of four 100 $\mu$g metered doses per day.

We have now surprisingly found that a lower metered unit dose of budesonide than that previously used can be administered safely and effectively to the nose.

DISCLOSURE OF THE INVENTION

According to the invention we provide a metered unit dose of a therapeutic composition comprising budesonide in therapeutically effective amount that is less than about 40 $\mu$g, said composition being suitable for nasal administration to a mammal in a single dose.

Preferably, the metered unit dose comprises from about 16 to about 40 $\mu$g of budesonide. In a preferred embodiment of the invention, the metered unit dose comprises about 32 $\mu$g of budesonide.

With this new lower metered unit dose, it is possible for the patient to take a lower metered daily dose, while still maintaining efficacy. The new lower unit dose is also convenient for the patient. Surprisingly, metered daily doses of 256 $\mu$g and 400 $\mu$g, delivered by nasal spray, were found to be equally efficacious. A metered daily dose of 256 $\mu$g can be obtained with a metered unit dose of 32 $\mu$g budesonide, dispensed 8 times daily (two doses in each nostril, twice a day).

A suitable pharmaceutical formulation of budesonide is a suspension of micronised budesonide in an aqueous vehicle.

Thus, the invention also comprises a unit dose, and preferably a metered unit dose, of a therapeutic composition comprising a therapeutically effective amount of budesonide that is less than about 40 $\mu$g, wherein the budesonide is in the form of finely divided particles and is suspended in an aqueous medium, said composition being suitable for administration to a mammal in a single dose.

Preferably, the unit dose formulation comprises from about 16 to about 40 $\mu$g of budesonide. In a most preferred embodiment of the formulation, the amount of budesonide is about 32 $\mu$g.

In a further aspect the invention comprises a suspension, preferably an aqueous suspension, comprising from about 0.6 to about 0.7 mg/ml (i.e. from about 0.06 to about 0.07% w/w) of budesonide.

In yet a further aspect the invention comprises a method of treating conditions of the nose of mammals by administering thereto a metered unit dose of 40 $\mu$g or less of budesonide.

Conditions that can be treated according to the invention include seasonal allergic rhinitis, i.e. pollinosis caused by pollens from ragweed, birch, grass, ceder or other plants perennial allergic rhinitis caused by e.g. dust mites (*Dermatophagoides pteronyssinus* and *D. farinae*), cockroaches and mammals such as cats, dogs and horses perennial non-allergic rhinitis nasal polyps, as well as prevention of post surgical nasal polyps chronic sinusitis recurrent sinusitis.

In order to form a stable suspension with a minimal tendency to agglomerate or form a sediment, a thickening agent may be included in the formulation. Examples of suitable thickening agents are microcrystalline cellulose, sodium carboxymethylcellulose, xanthan gum, carbomer, guar gum and hydroxypropyl cellulose. The thickening agent may be present at about 0.1 to 3.0% w/w of the formulation. Preferably microcrystalline cellulose and sodium carboxymethyl cellulose are present at about 0.5 to 2.5%, xanthan gum at about 0.3 to 3%, carbomer at about 0.1 to 2%, guar gum at about 0.3 to 2% and hydroxypropyl methyl cellulose at about 0.5 to 3.0%, w/w of the formulation.

Agents which make the suspension isotonic may be added. Examples are dextrose, glycerin, mannitol, sodium chloride and potassium chloride.

To obtain an efficient dispersion of the budesonide particles in the suspension, a surfactant may be used. Examples of suitable surfactants are Polysorbate 80 (Tween 80) as well as other polyoxyethylene sorbitan fatty acid esters, poloxamers, polyoxyethylene alkyl ethers and polyoxyethylene castor oil derivatives. The surfactant may be present at about 0.005 to 2% w/w of the formulation. We prefer the polyoxyethylene sorbitan fatty acid esters to be present at about 0.005 to 0.5%, poloxamers at about 0.01 to 2%, and polyoxyethylene alkyl ethers or the polyoxyethylene castor oil derivatives at about 0.01 to 1.0%, w/w of the formulation.

We also prefer the formulation to contain a suitable chelating agent, e.g. disodium edetate (EDTA). The chelating agent may be present at about 0.005 to 0.1% w/w of the formulation.

A preservative agent may be added to protect the formulation from microbial contamination. Examples of suitable preservatives are benzalkonium chloride, methylparaben, propylparaben, potassium sorbate and sodium benzoate. The preservative may be present at about 0.002 to 0.5% w/w of the formulation. Preferably benzalkonium chloride is present at about 0.002 to 0.02%, methylparaben at about 0.05 to 0.25%, propylparaben at about 0.01 to 0.2%, potassium sorbate at about 0.5 to 0.2%, and sodium benzoate at about 0.1 to 0.5%, w/w of the formulation.

The pH of the suspension may be adjusted as required. Examples of suitable pH regulating agents are strong mineral acids, e.g. hydrochloric acid. Alternatively, the pH of the system can be adjusted by balancing the acid and salt forms of preservative and chelating agent. We prefer the formulation to have a pH in the range 3.5 to 5.0 and more preferably from about 4.2 to 4.6.

The suspension medium is made essentially of purified water (as describe in the European Pharmacopoeia and the United States Pharmacopoeia), e.g. water for injection.

In the suspension the active constituent budesonide is present as small particles, where at least 90% of the small particles have a mass equivalent sphere diameter of less than 20 $\mu$m, preferably at least 80% less than 10 $\mu$m and most preferably at least 80% less than 7 $\mu$m.

The new unit dose can suitably be dispensed from the above mentioned specially adapted nasal inhaler or spray device. Other means for administration include a simple drop pipette or a rhinyl. Pre-compression metered-dose spray pumps with dose volumes from 25 $\mu$l to 150 $\mu$l can be used, whereby the concentration of budesonide in the suspension is adjusted to give the desired unit dose of budesonide. Monospray or a bispray pump can be used; for the latter, the recommended unit dose is sequentially delivered into each nostril, for a total metered dose per administration of less than 80 $\mu$g budesonide.

According to a further feature of the invention we also provide a therapeutic method of treating or preventing conditions of the upper respiratory tract, the method comprising metering into a nostril of a mammal a unit dose of budesonide, wherein said metered unit dose comprises budesonide in a therapeutically effective amount that is less than about 40 $\mu$g.

The metered amount of budesonide is preferably less than about 320 $\mu$g per day, delivered as 8 or more unit doses each dose comprising budesonide in an amount that is less than about 40 $\mu$g.

According to a yet further feature of the invention we provide a container containing budesonide and adapted to deliver a unit dose or a formulation according to the invention.

The invention will now be described more in detail in the following non-limiting examples.

EXAMPLE 1

A unit dose comprising a suspension of 32 $\mu$g budesonide in water was prepared by mixing the following ingredients:

| Ingredient | (mg) |
| --- | --- |
| Budesonide, micronised | 0.032 |
| Microcrystalline cellulose and carboxymethylcellulose Sodium (Avicel) | 0.625 |
| Dextrose, anhydrous | 2.375 |
| Polysorbate 80 | 0.008 |
| Edetate disodium | 0.005 |
| Potassium sorbate | 0.060 |
| Hydrochloric acid | to pH 4.5 |
| Purified water | to 50 $\mu$l (approx. 47.9 mg added) |

EXAMPLE 2

A 200 liter bulk suspension, which corresponds to approximately 23,000 containers with 120 doses (32 $\mu$g/dose) of budesonide each, was prepared by mixing the following ingredients:

| Ingredient | Amount (kg) |
| --- | --- |
| Budesonide, micronised | 0.128 |
| Microcrystalline cellulose and carboxymethylcellulose Sodium (Avicel) | 2.500 |
| Dextrose, anhydrous | 9.500 |
| Polysorbate 80 | 0.032 |
| Edetate disodium | 0.020 |
| Potassium sorbate | 0.240 |
| Hydrochloric acid | to pH 4.5 |
| Purified water | to 204.2 |

What is claimed is:

1. A unit dose of a therapeutic composition comprising about 16 to about 40 $\mu$g budesonide, wherein the budesonide
    (a) is in the form of finely divided particles, at least 90% of which have a mass equivalent sphere diameter of less than 20 $\mu$m, and
    (b) is suspended in an aqueous medium.

2. A therapeutic method of treating an inflammatory condition of the upper respiratory tract, the method comprising metering into the nose of a mammal in need thereof a therapeutically effective amount of budesonide that is less than about 320 $\mu$g per day, delivered as 8 or more unit doses in a metered amount of about 32 $\mu$g budesonide per unit dose, wherein each unit dose comprises finely divided budesonide particles, at least 90% of which have a mass equivalent sphere diameter of less than 20 $\mu$m, the particles being suspended in an aqueous medium.

3. The therapeutic method of claim 2, wherein at least 80% of the particles have a mass equivalent sphere diameter of less than 10 $\mu$m.

4. The therapeutic method of claim 2, wherein at least 80% of the particles have a mass equivalent sphere diameter of less than 7 $\mu$m.

5. The therapeutic method of claim 2, wherein the amount of budesonide is about 256 $\mu$g per day.

6. The therapeutic method of claim 2, wherein the concentration of budesonide in each unit dose is about 0.6 to 0.7 mg/ml.

7. A unit dose of a therapeutic composition consisting of (a) about 32 μg budesonide; and (b) other ingredients comprising
a mixture consisting of microcrystalline cellulose and sodium carboxymethyl cellulose, the mixture at about 0.5 to 2.5% by weight of the therapeutic composition;
dextrose;
Polysorbate 80 at about 0.005 to 0.5% by weight of the therapeutic composition;
disodium edetate at about 0.005 to 0.1% by weight of the therapeutic composition; and
potassium sorbate at about 0.05 to 0.2% by weight of the therapeutic composition,
wherein the budesonide is in the form of finely divided particles, at least 90% of which have a mass equivalent sphere diameter of less than 20 μm, suspended in an aqueous medium, said therapeutic composition being suitable for nasal administration to a mammal in a single dose.

8. The unit dose of claim 7, wherein at least 80% of the particles have a mass equivalent sphere diameter of less than 10 μm.

9. The unit dose of claim 7, wherein at least 80% of the particles have a mass equivalent sphere diameter of less than 7 μm.

10. A therapeutic method of treating an inflammatory condition of the upper respiratory tract, the method comprising metering into the nose of a mammal in need thereof a therapeutically effective amount of budesonide that is less than about 320 μg per day, delivered as 8 or more unit doses, wherein each unit dose consists of about 32 μg budesonide and other ingredients, the other ingredients comprising
a mixture consisting of microcrystalline cellulose and sodium carboxymethyl cellulose, the mixture at about 0.5 to 2.5% by weight of the therapeutic composition;
dextrose;
Polysorbate 80 at about 0.005 to 0.5% by weight of the therapeutic composition;
disodium edetate at about 0.005 to 0.1% by weight of the therapeutic composition; and
potassium sorbate at about 0.05 to 0.2% by weight of the therapeutic composition,
wherein the budesonide is in the form of finely divided particles, at least 90% having a mass equivalent sphere diameter of less than 20 μm, suspended in an aqueous medium.

11. The therapeutic method of claim 10, wherein at least 80% of the particles have a mass equivalent sphere diameter of less than 10 μm.

12. The therapeutic method of claim 10, wherein at least 80% of the particles have a mass equivalent sphere diameter of less than 7 μm.

13. The therapeutic method of claim 10, wherein the concentration of budesonide in each unit dose is about 0.6 to 0.7 mg/ml.

14. A therapeutic method of treating or preventing an inflammatory condition of the upper respiratory tract, the method comprising administering into a nostril of a mammal in need thereof a metered unit dose, the active ingredient of which consists of about 32 μg of budesonide formulated as finely divided particles, at least 90% of which have a mass equivalent sphere diameter of less than 20 μm, suspended in an aqueous medium.

15. The therapeutic method of claim 14, wherein at least 80% of the particles have a mass equivalent sphere diameter of less than 10 μm.

16. The therapeutic method of claim 14, wherein at least 80% of the particles have a mass equivalent sphere diameter of less than 7 μm.

17. The therapeutic method of claim 14, wherein the concentration of budesonide in the unit dose is about 0.6 to 0.7 mg/ml.

18. A therapeutic method of treating an inflammatory condition of the upper respiratory tract, the method comprising metering into the nose of a mammal in need thereof a therapeutically effective amount of budesonide that is less than about 320 μg per day, delivered as 8 or more unit doses, the active ingredient of each unit dose consisting of about 32 μg budesonide formulated as finely divided particles, at least 90% of which have a mass equivalent sphere diameter of less than 20 μm, suspended in an aqueous medium.

19. The therapeutic method of claim 18, wherein at least 80% of the particles have a mass equivalent sphere diameter of less than 10 μm.

20. The therapeutic method of claim 18, wherein at least 80% of the particles have a mass equivalent sphere diameter of less than 7 μm.

21. The therapeutic method of claim 18, wherein the concentration of budesonide in each unit dose is about 0.6 to 0.7 mg/ml.

22. A unit dose of a therapeutic composition, the active ingredient of which consists of about 32 μg budesonide, wherein the therapeutic composition additionally comprises
a mixture consisting of microcrystalline cellulose and sodium carboxymethyl cellulose, the mixture at about 0.5 to 2.5% by weight of the therapeutic composition;
dextrose;
Polysorbate 80 at about 0.005 to 0.5% by weight of the therapeutic composition;
disodium edetate at about 0.005 to 0.1% by weight of the therapeutic composition; and
potassium sorbate at about 0.05 to 0.2% by weight of the therapeutic composition,
wherein the budesonide is in the form of finely divided particles, at least 90% of which have a mass equivalent sphere diameter of less than 20 μm, suspended in an aqueous medium, said therapeutic composition being suitable for nasal administration to a mammal in a single dose.

23. The unit dose of claim 22, wherein at least 80% of the particles have a mass equivalent sphere diameter of less than 10 μm.

24. The unit dose of claim 22, wherein at least 80% of the particles have a mass equivalent sphere diameter of less than 7 μm.

25. The unit dose of claim 22, wherein the concentration of budesonide in the unit dose is about 0.6 to 0.7 mg/ml.

26. A unit dose of a therapeutic composition comprising about 32 μg budesonide, wherein the budesonide is in the form of finely divided particles, at least 90% of which have a mass equivalent sphere diameter of less than 20 μm, and is suspended in an aqueous medium having a pH between 3.5 and 5.0, said composition being suitable for administration to a mammal in a single dose, wherein the composition includes no more than about 32 μg budesonide.

27. The unit dose of claim 26, wherein the pH of the aqueous medium is between 4.2 and 4.6.

28. The unit dose of claim 26, wherein the composition is suitable for nasal administration to a mammal.

29. The unit dose of claim 26, wherein the concentration of budesonide in the composition is about 0.6 to 0.7 mg/ml.

30. The unit dose of claim 26, further comprising one or more pharmaceutically acceptable additives selected from the group consisting of thickening agents, isotonicity agents, surfactants, chelating agents, and preservatives.

31. A therapeutic method of treating or preventing an inflammatory condition of the upper respiratory tract, the method comprising administering into a nostril of a mammal in need thereof a metered unit dose of finely divided budesonide particles, at least 90% of which have a mass equivalent sphere diameter of less than 20 µm, suspended in an aqueous medium having a pH between 3.5 and 5.0, wherein said metered unit dose consists of about 32 µg budesonide and one or more ingredients other than budesonide.

32. The therapeutic method of claim 31, wherein the pH of the aqueous medium is between 4.2 and 4.6.

33. The therapeutic method of claim 31, wherein the condition to be treated is seasonal allergic rhinitis.

34. The therapeutic method of claim 31, wherein the condition to be treated is perennial allergic rhinitis.

35. The therapeutic method of claim 31, wherein the condition to be treated is perennial non-allergic rhinitis.

36. The therapeutic method of claim 31, wherein the condition to be treated is chronic sinusitis.

37. The therapeutic method of claim 31, wherein the condition to be treated is recurrent sinusitis.

38. The therapeutic method of claim 31, wherein the condition to be treated is nasal polyps.

39. The therapeutic method of claim 31, wherein the concentration of budesonide in the unit dose is about 0.6 to 0.7 mg/ml.

40. A therapeutic method of treating an inflammatory condition of the upper respiratory tract, the method comprising metering into the nose of a mammal in need thereof a therapeutically effective amount of budesonide that is less than about 320 µg per day, delivered as 8 or more unit doses in a metered amount of about 32 µg budesonide per unit dose, wherein each unit dose comprises finely divided budesonide particles, at least 90% of which have a mass equivalent sphere diameter of less than 20 µm, suspended in an aqueous medium having a pH between 3.5 and 5.0.

41. The therapeutic method of claim 40, wherein the pH of the aqueous medium is between 4.2 and 4.6.

42. A therapeutic method according to claim 40, wherein the amount of budesonide is about 256 µg per day.

43. The therapeutic method of claim 40, wherein the concentration of budesonide in each unit dose is about 0.6 to 0.7 mg/ml.

44. A unit dose of a therapeutic composition consisting of (a) about 32 µg budesonide; and (b) other ingredients comprising
 a mixture consisting of microcrystalline cellulose and sodium carboxymethyl cellulose, the mixture at about 0.5 to 2.5% by weight of the therapeutic composition;
 dextrose;
 Polysorbate 80 at about 0.005 to 0.5% by weight of the therapeutic composition;
 disodium edetate at about 0.005 to 0.1% by weight of the therapeutic composition; and
 potassium sorbate at about 0.05 to 0.2% by weight of the therapeutic composition,
 wherein the budesonide is in the form of finely divided particles, at least 90% of which have a mass equivalent sphere diameter of less than 20 µm, suspended in an aqueous medium having a pH between 3.5 and 5.0, said therapeutic composition being suitable for nasal administration to a mammal in a single dose.

45. The unit dose of claim 44, wherein the pH of the aqueous medium is between 4.2 and 4.6.

46. A therapeutic method of treating an inflammatory condition of the upper respiratory tract, the method comprising metering into the nose of a mammal a therapeutically effective amount of budesonide that is less than about 320 µg per day, delivered as 8 or more unit doses, wherein each unit dose consists of about 32 µg budesonide and other ingredients, the other ingredients comprising
 a mixture consisting of microcrystalline cellulose and sodium carboxymethyl cellulose, the mixture at about 0.5 to 2.5% by weight of the therapeutic composition;
 dextrose;
 Polysorbate 80 at about 0.005 to 0.5% by weight of the therapeutic composition;
 disodium edetate at about 0.005 to 0.1% by weight of the therapeutic composition; and
 potassium sorbate at about 0.05 to 0.2% by weight of the therapeutic composition,
 wherein the budesonide is in the form of finely divided particles, at least 90% of which have a mass equivalent sphere diameter of less than 20 µm, suspended in an aqueous medium having a pH between 3.5 and 5.0.

47. The therapeutic method of claim 46, wherein the pH of the aqueous medium is between 4.2 and 4.6.

48. The therapeutic method of claim 46, wherein the concentration of budesonide in each unit dose is about 0.6 to 0.7 mg/ml.

49. A unit dose of a therapeutic composition, the active ingredient of which consists of about 32 µg budesonide formulated as finely divided particles, at least 90% of which have a mass equivalent sphere diameter of less than 20 µm, suspended in an aqueous medium having a pH between 3.5 and 5.0, said composition being suitable for administration to a mammal in a single dose.

50. The unit dose of claim 49, wherein the pH of the aqueous medium is between 4.2 and 4.6.

51. The unit dose of claim 49, wherein the concentration of budesonide in the composition is about 0.6 to 0.7 mg/ml.

52. A therapeutic method of treating or preventing an inflammatory condition of the upper respiratory tract, the method comprising administering into a nostril of a mammal a metered unit dose, the active ingredient of which consists of about 32 µg of budesonide formulated as finely divided particles, at least 90% of which have a mass equivalent sphere diameter of less than 20 µm, suspended in an aqueous medium, having a pH between 3.5 and 5.0.

53. The therapeutic method of claim 52, wherein the pH of the aqueous medium is between 4.2 and 4.6.

54. The therapeutic method of claim 52, wherein the concentration of budesonide in the unit dose is about 0.6 to 0.7 mg/ml.

55. A therapeutic method of treating an inflammatory condition of the upper respiratory tract, the method comprising metering into the nose of a mammal a therapeutically effective amount of budesonide that is less than about 320 µg per day, delivered as 8 or more unit doses, the active ingredient of each unit dose consisting of about 32 µg budesonide formulated as finely divided particles, at least 90% of which have a mass equivalent sphere diameter of less than 20 µm, suspended in an aqueous medium having a pH between 3.5 and 5.0.

56. The therapeutic method of claim 55, wherein the pH of the aqueous medium is between 4.2 and 4.6.

57. The therapeutic method of claim 55, wherein the concentration of budesonide in each unit dose is about 0.6 to 0.7 mg/ml.

58. A unit dose of a therapeutic composition, the active ingredient of which consists of about 32 µg budesonide, wherein the therapeutic composition additionally comprises
a mixture consisting of microcrystalline cellulose and sodium carboxymethyl cellulose, the mixture at about 0.5 to 2.5% by weight of the therapeutic composition;
dextrose;
Polysorbate 80 at about 0.005 to 0.5% by weight of the therapeutic composition;
disodium edetate at about 0.005 to 0.1% by weight of the therapeutic composition; and
potassium sorbate at about 0.05 to 0.2% by weight of the therapeutic composition,
wherein the budesonide is in the form of finely divided particles, at least 90% of which have a mass equivalent sphere diameter of less than 20 µm, suspended in an aqueous medium having a pH between 3.5 and 5.0, said therapeutic composition being suitable for nasal administration to a mammal in a single dose.

59. The unit dose of claim 58, wherein at least 80% of the particles have a mass equivalent sphere diameter of less than 10 µm.

60. The unit dose of claim 58, wherein at least 80% of the particles have a mass equivalent sphere diameter of less than 7 µm.

61. The unit dose of claim 58, wherein the concentration of budesonide in the composition is about 0.6 to 0.7 mg/ml.

62. A container containing budesonide and adapted to deliver the unit dose of claim 7.

63. A container containing budesonide and adapted to deliver the unit dose of claim 8.

64. A container containing budesonide and adapted to deliver the unit dose of claim 9.

65. A container containing budesonide and adapted to deliver the unit dose of claim 26.

66. A container containing budesonide and adapted to deliver the unit dose of claim 27.

67. A container containing budesonide and adapted to deliver the unit dose of claim 44.

68. A container containing budesonide and adapted to deliver the unit dose of claim 45.

69. The method of claim 2, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

70. The method of claim 10, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

71. The method of claim 14, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

72. The method of claim 70, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

73. The method of claim 31, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

74. The method of claim 40, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

75. The method of claim 46, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

76. The method of claim 52, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

77. The method of claim 55, wherein the inflammatory condition of the upper respiratory tract is selected from the group consisting of seasonal allergic rhinitis, perennial allergic rhinitis, perennial non-allergic rhinitis, nasal polyps, chronic sinusitis, and recurrent sinusitis.

* * * * *

UNITED STATES PATENT AND TRADEMARK OFFICE
CERTIFICATE OF CORRECTION

PATENT NO. : 6,986,904 B2
DATED : January 17, 2006
INVENTOR(S) : Hans Nilsson and Gordon Santesson It is certified that error appears in the above-identified patent and that said Letters Patent is hereby corrected as shown below:

Column 10,
Line 13, "70" should be -- 18 --.

Signed and Sealed this

Eighteenth Day of April, 2006

JON W. DUDAS
*Director of the United States Patent and Trademark Office*